Jan. 9, 1968 O. F. TATE Plant Pat. 2,787
ROSE PLANT
Filed Oct. 4, 1966
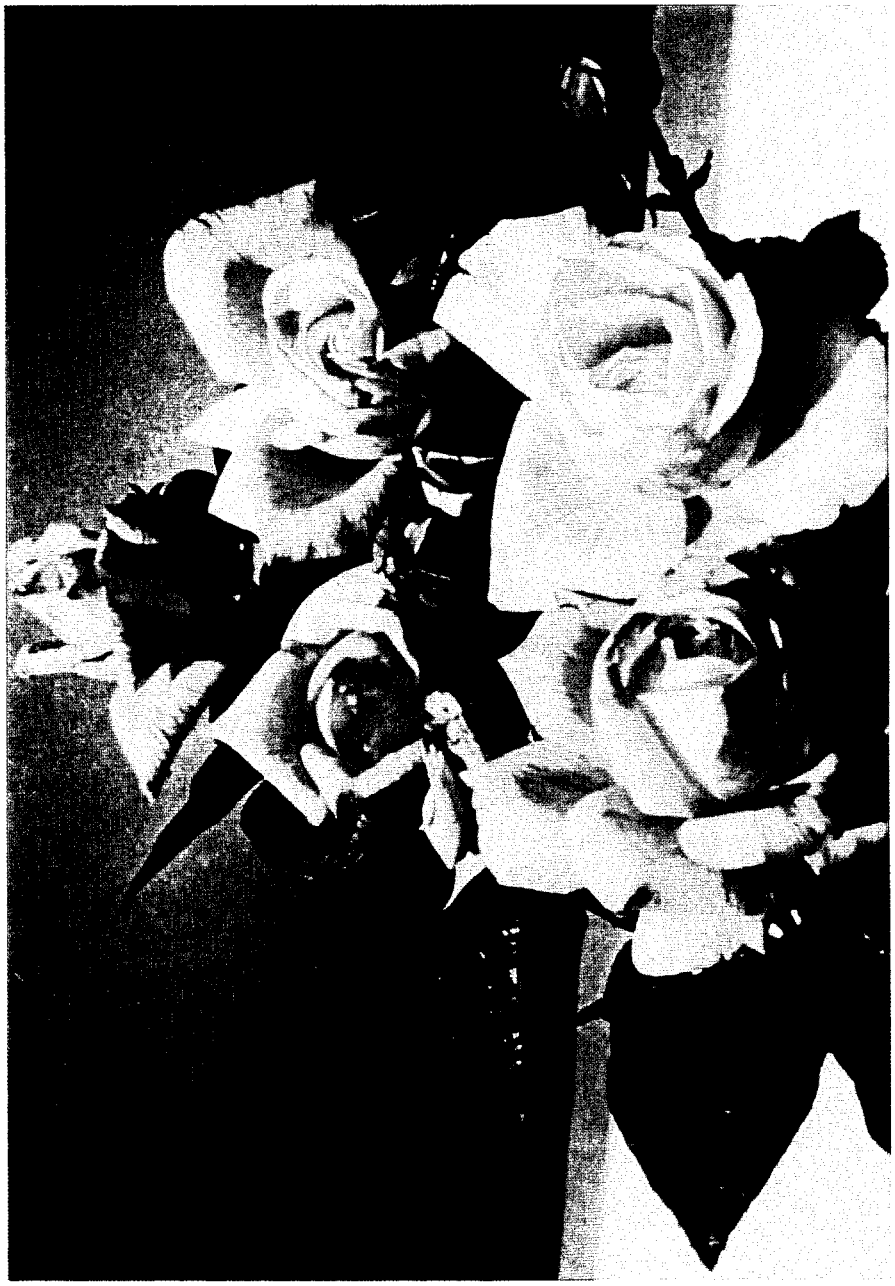
Inventor.
Otis F. Tate
By: Robb & Robb
Attorneys.

United States Patent Office

Plant Pat. 2,787
Patented Jan. 9, 1968

2,787
ROSE PLANT

Otis F. Tate, Tyler, Tex., assignor to Texas Rose Research Foundation, Inc., Tyler, Tex., a corporation of Texas Filed Oct. 4, 1966, Ser. No. 585,713
1 Claim. (Cl. Plt.—11)

The present invention relates to a new and distinct variety of rose plant of the hybrid tea class, which was discovered by me in my nursery at Tyler, Tex., as a cultivated sport of the rose variety known as "Peace" (Plant Patent No. 591).

At the time of my discovery aforementioned, I was growing the variety "Peace" in the fields of my nursery, and my attention was attracted to one particular plant having one stem on which the flowers differed in color from those of all other plants of "Peace" in that field. Upon close inspection of this particular plant, I found that it had sported, and I thereupon took steps to preserve the sport, keep it under close observation, and promptly propagated the same by budding, as performed by me in my nursery fields aforesaid. Continued observations of the original sport and the progeny thereof convinced me that the sport definitely represented a new and distinct variety, differing from its parent, as well as from all other varieties of which I am aware, as evidenced by its general similarity to the variety "Peace," but bearing flowers which are Brilliant Yellow in general color tonality, with an unusual, distinctive and attractive vein coloration varying from Deep Pink to Strong Red, and the colors being more intense at the outer edges of the flower petals.

The accompanying drawing shows typical specimens of the vegetative growth and flowers of my new variety in different stages of development and as depicted in color as nearly true as it reasonably possible to make the same in a color illustration of this character.

The following is a detailed description of my new rose variety, with color terminology in accordance with the Nickerson Color Fan, published by Munsell Color Company, of Baltimore, Md., except where general color terms of ordinary dictionary significance are obvious:

Type: Hardy; bush; outdoor; sport; for garden decoration.
Class: Hybrid tea.
Parentage: Sport of "Peace."
Propagation: Holds its distinguishing characteristics through succeeding propagations by budding.

*Flower*

Locality where grown and observed: Tyler, Tex.
Flowers borne: Singly; on strong and medium long stems.
Quantity of bloom: Abundant, outdoors.
Continuity: Continuous.
Fragrance: Moderate. Nature—tea.
Bud:
*Peduncle.*—Medium long; heavy; erect; stiff; rough. Color—dark green.
*Before calyx breaks.*—Size—large. Form—globular; with a conspicuous neck; with foliaceous appendages on the surface of the bud; with bristle-like parts extending beyond the tip of the bud equal to ¼ of its length. Color—sepals of Strong Green, Plate 5G 5/8 which surround the bud.
*As calyx breaks.*—Color—Brilliant Yellow, Plate 5Y 9/9, with veins from Deep Pink, Plate 2.5R 6/11 to Strong Red, Plate 2.5R 5/12.
*As first petal opens.*—Size—large. Form—ovoid-globular. Color: outside—Brilliant Yellow, Plate 5Y 9/9, with veins from Deep Pink, Plate 2.5R 6/11 to Strong Red, Plate 2.5R 5/12; inside—Brilliant Yellow, Plate 5Y 9/9, with veins from Deep Pink, Plate 2.5R 6/11 to Strong Red, Plate 2.5R 5/12.
*Opening.*—Opens up well.
Bloom:
*Size (when fully open).*—Large; from 4 inches to 6 inches.
*Petalage.*—Very double; from 40 to 60 petals; arranged regularly.
*Form.*—Cupped, high-centered and globular at first, but becoming cupped and high-centered; petals being at first cupped outward, but becoming cupped and rolled outward at maturity.
Petals:
*Texture.*—Leathery.
*Appearance.*—Inside—satiny. Outside—satiny.
*Shape.*—Outside—obovate. Intermediate—obovate. Inside—obovate.

This description of a newly opened flower was made from a rose grown outdoors during the month of June at Tyler, Tex.:

*Color.*—Outer, intermediate and inner petals—outside and inside surfaces—Brilliant Yellow, Plate 5Y 9/9, with veins from Deep Pink, Plate 2.5R 6/11 to Strong Red, Plate 2.5R 5/12.

This description was made from a rose that was open for three days outdoors during the month of August at Tyler. Tex.:

*Color.*—Outer, intermediate and inner petals—outside and inside surfaces—Brilliant Yellow, Plate 5Y 9/9, with veins from Deep Pink, Plate 2.5R 6/11 to Strong Red, Plate 2.5R 5/12.
*General color effect.*—Brilliant Yellow, Plate 5Y 9/9, with veins from Deep Pink, Plate 2.5R 6/11 to Strong Red, Plate 2.5R 5/12.
*Behavoir.*—Drop off cleanly; most intense color in autumn season.
*Flower longevity.*—On bush in garden—4 days in June. Cut roses grown outdoors and kept at living room temperatures—5 days in June.

*Reproductive organs*

Stamens: Many; arranged irregularly about pistils.
Filaments: From short to long; most with anthers. Color—Reddish-Orange, Plate 10R 4/9.
Anthers: Medium size; open at various times. Color—Yellow, Plate 2.5Y 9/9.
Pollen: Abundant. Color—yellow.
Pistils: Many.
Styles: Medium length; thin; bunched.
Stigma: Color—Yellow, Plate 2.5Y 9/9.
Ovaries: Enclosed in calyx.
Hips: Short, pointed; with a conspicuous neck; pear-shaped; smooth; walls thick and fleshy. Color—Brilliant Yellowish-Green, Plate 10GY 7/8.
Sepals: Falling soon; from moderate length to long; spear-shaped; recurved.
Seeds: Few; medium large size.

*Plant*

Foliage:
*Leaves.*—Compound of 5 leaflets; normal abundance; large; leathery; glossy.
*Leaflets.*—Shape—oval. Apex—acute. Base—round. Margin—serrate.
*Color.*—Mature: upper surface—dark green; under surface—light green. Young: upper surface—dark green; under surface—light green.

*Rachis (the supporting stem of the compound leaf.)*—Medium heavy. Upper side—smooth; grooved. Under side—sparsely prickly and thorny.

*Stipules.*—Medium long; medium wide; with moderately long points turning out at an angle of less than 45°.

*Disease and insect resistance.*—Similar to "Peace," as determined by comparison with that variety grown under the same conditions at Tyler, Tex.

Growth:

*Habit.*—Upright; much-branched.

*Growth.*—Vigorous.

*Canes.*—Moderately heavy.

*Main stems.*—Color—Green, Plate 10GY 6/9. Thorns—several; medium long; some straight and some hooked downward; with narrow base. Prickles—none. Hairs—none.

*Branches.* — Color — Green, Plate 10GY 6/9. Thorns—several; medium long; hooked downward; with narrow base. Prickles—none. Hairs—none.

*New shoots.*—Color—Green, Plate 10GY 6/9. Thorns—many; medium long; hooked downward; with narrow base. Prickles—none. Hairs—none.

I claim:

1. A new and distinct variety of rose plant of the hybrid tea class, substantially as herein shown and described, characterized particularly as to novelty by its general similarly to the parent variety "Peace" (Plant Patent No. 591), but bearing flowers which are Brilliant Yellow in general color tonality, with an unusual, distinctive and attractive vein coloration varying from Deep Pink to Strong Red, and the colors being more intense at the outer edges of the flower petals.

No references cited.

ROBERT E. BAGWILL, *Primary Examiner.*